United States Patent [19]
Katayama et al.

[11] Patent Number: 4,672,561
[45] Date of Patent: Jun. 9, 1987

[54] ENTHALPY CALCULATOR UNIT

[75] Inventors: Akifumi Katayama, Fujisawa; Keijirou Mori, Kouza; Satoshi Ueda, Kamakura; Katsuhiko Suwa, Moriguchi, all of Japan

[73] Assignee: Matsushita Electric Industrial Co., Ltd., Osaka, Japan

[21] Appl. No.: 852,082

[22] Filed: Apr. 14, 1986

Related U.S. Application Data

[63] Continuation-in-part of Ser. No. 536,153, Aug. 26, 1983, abandoned.

[30] Foreign Application Priority Data

Feb. 15, 1982 [JP] Japan ............................. 57-22317
Feb. 14, 1983 [WO] CT Int'l Appl. ..... PCT/JP83/00043

[51] Int. Cl.$^4$ .......................................... G01K 17/00
[52] U.S. Cl. ..................... 364/556; 73/336; 374/35; 374/31; 374/170
[58] Field of Search ................. 364/551, 556; 73/112, 73/115, 336; 374/31, 35, 170; 236/44 R, 44 C

[56] References Cited

U.S. PATENT DOCUMENTS

| | | | |
|---|---|---|---|
| 3,422,675 | 1/1969 | Shannon et al. | 374/35 |
| 3,866,026 | 2/1975 | de Viry | 364/556 |
| 4,078,431 | 3/1978 | Mott | 374/31 |
| 4,182,180 | 1/1980 | Mott | 73/336 |
| 4,319,485 | 3/1982 | Terada et al. | 73/336 |
| 4,380,155 | 4/1983 | Paddock et al. | 374/170 |
| 4,558,595 | 12/1985 | Kompelien | 73/336 |

FOREIGN PATENT DOCUMENTS

| | | | |
|---|---|---|---|
| 0157677 | 12/1979 | Japan | 73/336 |
| 0120157 | 7/1983 | Japan | 374/35 |

Primary Examiner—Parshotam S. Lall
Attorney, Agent, or Firm—Wenderoth, Lind & Ponack

[57] ABSTRACT

An enthalpy calculator unit outputs a value of enthalpy directly from two measured parameters, such as dry bulb temperature and relative humidity, and includes a humidity sensor 17 for converting a measured relative humidity into an electrical signal; temperature sensors for converting a measured temperature into electrical signals; and arithmetic units for calculating the enthalpy and for outputting electrical signal corresponding thereto after performiing a calculation based on the signals input by the sensors in accordance with the following equation:

$$i = (ae^{bt} - c)(t+d)\psi + mt + n$$

where
a, b, c, d, m, and n are constants, and:
t: dry bulb temperature (°C.)
$\psi$: relative humidity (%), and a, b, c, d, m, and n are selected so that $|i - i_0| \leq 0.5$ within a fixed temperture range if:

$$i_0 = 0.240t + (597.3 + 0.441t)x$$

$$x = 0.622 \cdot \psi \cdot h / (P - \psi \cdot h)$$

where
P: atmospheric pressure
h: saturated vapor pressure under the atomspheric pressure P.

1 Claim, 11 Drawing Figures

ENTHALPY CALCULATOR UNIT

This application is a continuation-in-part of now abandoned application Ser. No. 536,153, filed Aug. 26, 1983.

BACKGROUND OF THE INVENTION

This invention relates to an enthalpy calculator unit in which enthalpy is calculated by an arithmetic unit in accordance with an enthalpy equation from the temperature and relative humidity of humid air. The calculated enthalpy is converted into electrical signals which are subsequently output.

The enthalpy of humid air may be calculated from the following equations (A) and (B) when the temperature and pressure thereof are within the ranges in which every-day air conditioning units operate.

$$i = 0.240t + (597.3 + 0.441t)x \quad (A)$$

$$x = 0.622 h_S \cdot \psi / P - h_S \cdot \psi \quad (B)$$

where
- t: dry bulb temperature (°C.),
- x: humidity ratio (kg/kg'),
- P: atmospheric pressure (mmHg),
- $h_S$: saturated vapor pressure (mmHg),
- $\psi$: relative humidity (%),
- i: enthalpy (Kcal/kg').

With equation (B), a complicated calculation is needed in which a value obtained by an approximate expression that has hitherto been disclosed, such as the IFC (International Formulation Committee) Formulation for Industrial Use must be substituted therein to obtain the saturated vapor pressure.

Accordingly, to obtain a value for the enthalpy of humid air using a conventional arithmetic unit, it has been necessary to obtain one other measured value, in addition to the dry bulb temperature. That is to say, conventional methods depend on the humidity ratio, wet bulb temperature, relative humidity, and dew point temperature and, whichever method is used, the measured values are used to calculate the enthalpy in accordance with equations (A) and (B) with an electronic computer. Any method depending on finding the dew point temperature or the humidity ratio has drawbacks including: a slow reaction speed and expensive sensing elements, and other methods depending on the wet bulb temperature, relative humidity, and dew point temperature having a disadvantage in that complicated equations must be solved.

SUMMARY OF THE INVENTION

According to this invention, the value of enthalpy is calculated by an arithmatic unit for performing calculations using the following enthalpy calculations equation (C), when a limitation is imposed on the range of temperature (about 20°-30° C.) of air in a room when air conditioning is provided. Using this equation, a calculated value of enthalpy can be obtained $$i = (ae^{bt} - c)(t + d)\psi + mt + n \quad (C)$$

where a, b, c, d, m and n are all constants.

By using equation (C) according to this invention, a value of enthalpy which is more accurate than that read from psychrometric diagram can be found easily without performing the conventional complicated calculations based on equations (A) and (B), provided that the temperature at which the enthalpy is calculated is within the temperature range used in practice.

The method of deriving equation (C) will now be described.

It is difficult to express enthalpy by a simple relationship depending on relative humidity and dry bulb temperature when using a psychrometric diagram (i−x diagram) and the fundamental equations (A) and (B) for the enthalpy calculation; however, it can be approximated by a linear function of the relative humidity $\psi$ and can be expressed by the following equation (D) when the dry bulb temperature is kept constant as shown in FIG. 1.

$$i = \alpha \psi + \beta \quad (D)$$

where $\alpha$ and $\beta$ are constants. These constants $\alpha$ and $\beta$ can be expressed by approximate expressions (E) and (F), respectively, as linear functions of the temperature t within a narrow range of temperature centered on a specific temperature point (for example, ±1° C.) as shown in FIGS. 2 and 3.

$$\alpha = Pt + q = P(t + q/P) \quad (E)$$

$$\beta = rt + s \quad (F)$$

By applying equations (E) and (F) to each range of temperature centered on a specific temperature and examining the variations in the coefficients, it has been discovered that P can be expressed approximately by the following exponential equation (G) (shown in FIG. 4); q/P, by a linear equation (H) (shown in FIG. 5); and $\beta$, by a linear equation (I) (shown in FIG. 6) within a comparatively wide range of temperatures.

$$P = A \cdot e^{Bt} + C \quad (G)$$

$$q/P = Dt + E \quad (H)$$

$$\beta = mt + n \quad (I)$$

When equations (G), (H), and (I) are substituted into equations (E) and (F), and the results thereof are then substituted into equation (D), another equation (J) can be obtained as follows:

$$i = (a \cdot e^{bt} - c)(t + d) \cdot \psi + mt + n \quad (J)$$

The following equation (K) is obtained by applying equation (J) to the temperature range of 5° to 35° C.

$$i = (2.059 \times 10^{-4} \cdot e^{0.05267t} - 5.2755 \times 10^{-5}) \cdot (t + 145.81)\psi + 0.2326t + 0.1054 \quad (K)$$

A method of obtaining equation (K) will now be described. When the dry bulb temperature is kept constant in the fundamental equations (A) and (B), the relationship between the relative humidity $\psi$ and the enthlapy i can be approximated by a linear function from enthalpy values when the relative humidity is either 30 or 70%. If a calculation is then performed using equations (E) and (F) and if an approximate expression is assumed within the temperature range of, for example ±1° C. centered on a dry bulb temperature of 20° C., the relationship between the enthalpy i and the relative humidity at $t_1=19°$ C. and $t_2=21°$ C. can be approximated by the linear expression (D).

$$i=0.08345\psi+4.5215 \text{ at } t_1=19° \text{ C.}$$

$$i=0.09485\psi+4.9915 \text{ at } t_2=21° \text{ C.}$$

If $\alpha$ and $\beta$ are approximated by linear functions of temperature, the following are obtained:

$$\alpha=5.707\times10^{-3}t-0.02500 \quad (L)$$

$$\beta=0.2346t+0.06545 \quad (M)$$

In the same way, $\alpha$ and $\beta$ are calculated for central temperatures of 5, 10, 15, 25, 30, and 35° C., and the coefficients P, q/P, and $\beta$ are obtained by the method of least squares from equations (G), (H), and (I) as follows:

$$P=2.1860\times10^{-3}\cdot e^{0.05267t}-5.6\times10^{-4} \quad (N)$$

$$q/P=-0.9058t+13.7359 \quad (O)$$

$$\beta=0.2326t+0.1054 \quad (P)$$

Equation (K) is obtained from the above three equations. An accuracy comparison between equation (K) and the fundamental equations (A) and (B) is shown in Table 1, wherein the difference in enthalpy therebetween is not larger than 0.5 over a wide temperature range, and the accuracy of the values in Table 1 is high enough for use within the ranges of temperature and relative humidity used in practice.

TABLE 1

| Relative tempera-ture (%) | Temperature (°C.) | | | | | | |
|---|---|---|---|---|---|---|---|
| | 5 | 10 | 15 | 20 | 25 | 30 | 35 |
| 10 | 0.072 | 0.039 | 0.006 | −0.023 | −0.043 | −0.048 | −0.023 |
| 20 | 0.075 | 0.045 | 0.016 | −0.007 | −0.015 | 0.007 | 0.083 |
| 30 | 0.077 | 0.050 | 0.024 | 0.005 | 0.006 | 0.048 | 0.166 |
| 40 | 0.079 | 0.054 | 0.029 | 0.013 | 0.020 | 0.076 | 0.223 |
| 50 | 0.080 | 0.057 | 0.033 | 0.017 | 0.026 | 0.089 | 0.256 |
| 60 | 0.080 | 0.058 | 0.034 | 0.016 | 0.024 | 0.089 | 0.263 |
| 70 | 0.080 | 0.059 | 0.033 | 0.012 | 0.014 | 0.074 | 0.244 |
| 80 | 0.080 | 0.058 | 0.030 | 0.003 | −0.003 | 0.044 | 0.199 |
| 90 | 0.079 | 0.057 | 0.024 | −0.010 | −0.029 | −0.000 | 0.126 |

DESCRIPTION OF THE PREFERRED EMBODIMENT

Figure 1:
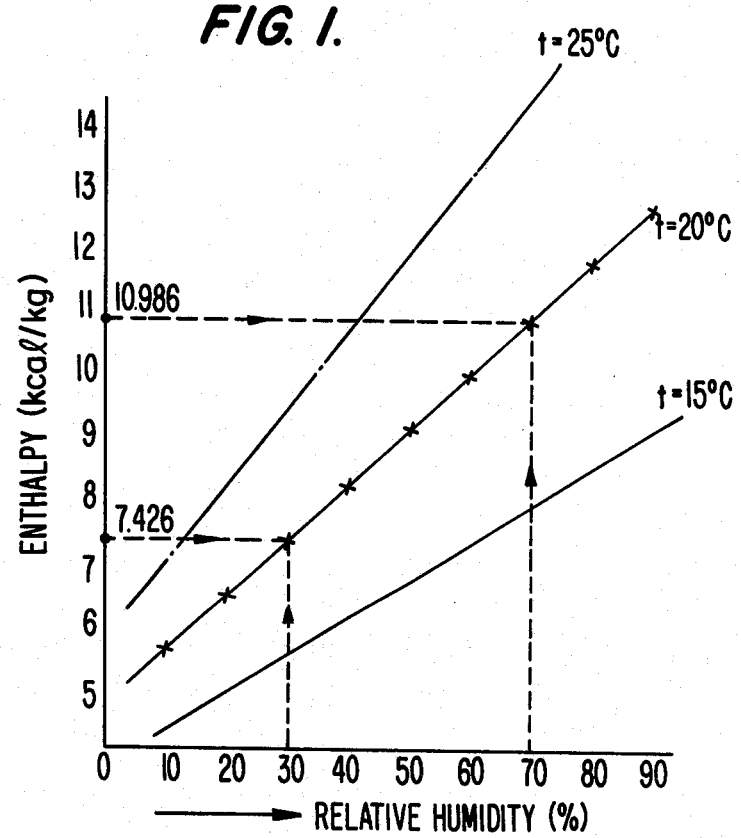
FIG. 1 is a graph of the relationship between relative humidity and enthalpy.
Figure 2:
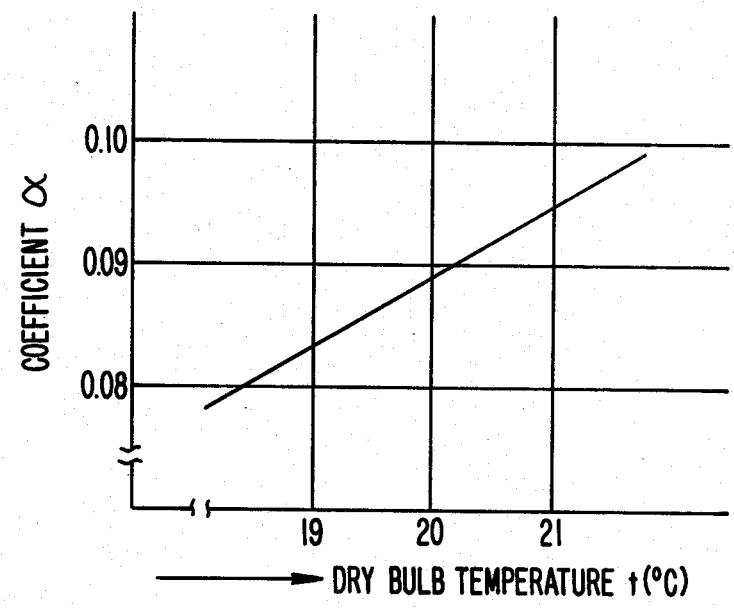
FIG. 2 is a graph of the relationship between dry bulb temperature and the coefficient $\alpha$.
Figure 3:
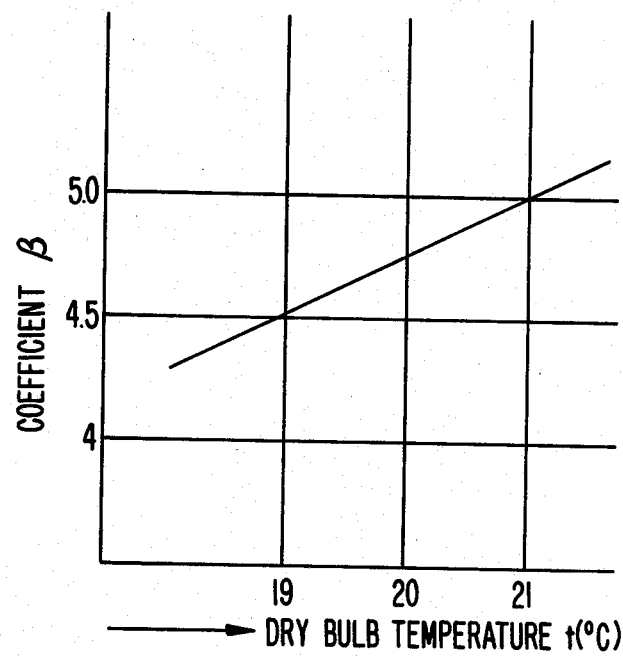
FIGS. 3 and 6 are graphs of the relationship between dry bulb temperature and the coefficient $\beta$.
Figure 4:
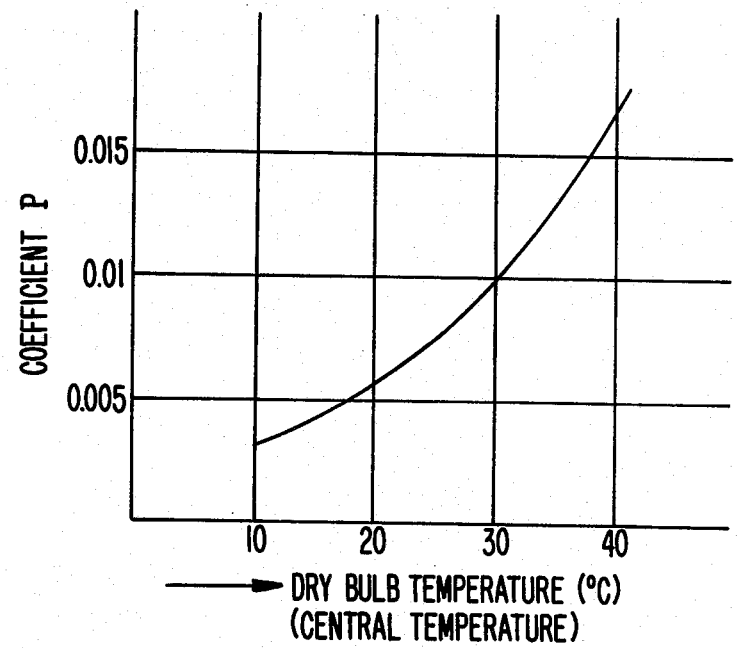
FIGS. 4 and 5 are graphs of the relationship between dry bulb temperature and the coefficients P and q/P; and, FIG. 7 is a circuit diagram of an embodiment of this invention.
Figure 5:
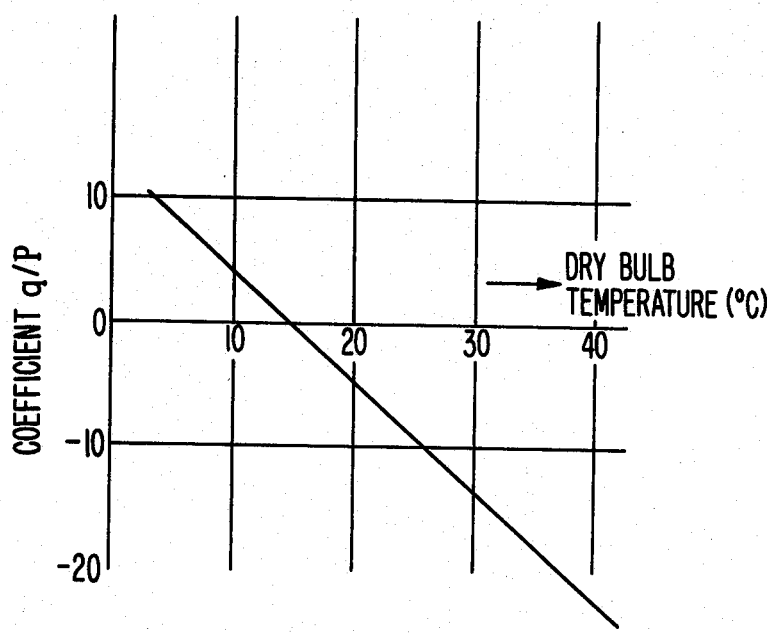
Figure 6:
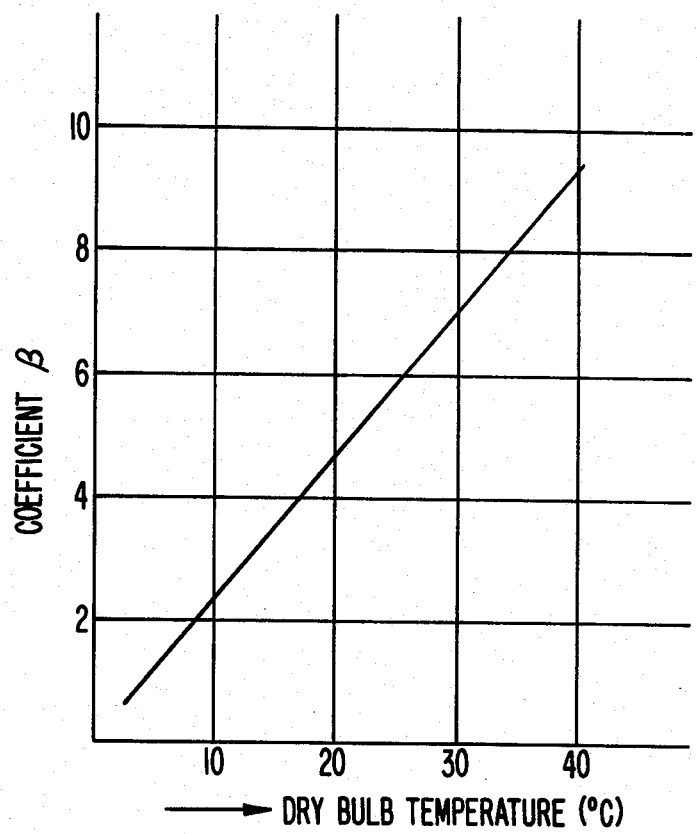

An embodiment of this invention, which performs a calculation in accordance with equation (I) will be described with reference to FIG. 7. Reference character A denotes a temperature signal output section. Numeral 1 represents a combined resistance comprising a temperature sensor 2 which senses variations in temperature as variations in electrical resistance. The voltage at a terminal 3 is obtained from the voltage between terminals 4 and 5 divided by the ratio of the resistances of resistors 1 and 6, and can be expressed by the resistance of the temperature sensor 2, that is, as a linear function of temperature. Reference character B indicates a conversion section which outputs a voltage proportional to an input voltage used as a power of an exponential function. When the collector of a transistor 8 is connected to an inverting input terminal of an operational amplifier 7, a voltage expressed as an exponential function whose power corresponds to the input voltage, i.e., the base-emitter voltage, is output from an output terminal 9 of the operational amplifier since the collector current of the transistor 8 is an exponential function of the base-emitter voltage. By providing a voltage output section 10 in a negative feedback circuit of the amplifier 7, a voltage correction corresponding to the constant c in equation (J) can be performed.

A multiplier section C multiplies a term including an exponential function whose power varies with temperature by a linear function whose variable is temperature. When a combined resistance 13 comprising a temperature sensor 12, which senses temperature variations and converts them to resistance variations which are expressed by a linear function whose variable is temperature, is located in the negative feedback circuit 11, and the amplification of the operational amplifier is determined by the ratio of resistances 13 and 14, and the voltage at an output terminal 15 of the amplifier 11 is proportional a product of the voltage at the terminal 9 and the resistance 13. A multiplier section D for the humidity signal, comprises a temperature sensor 17, which senses humidity variations and converts them to resistance variations is located in the negative feedback circuit of an operational amplifier 16, wherein, by providing a combined resistance 18 having resistance variations expressed as a linear function whose variable is humidity, the voltage at a output terminal 19 of the section D is proportional to the product of the voltage at terminal 15 and the resistance 18. Section E is an output section for the temperature signal, a combined resistance 20 thereof comprises a temperature sensor resistor 21 that senses temperature variations and converts them to resistance variations. The voltage at a terminal 22 is obtained by dividing the voltage at a terminal 23 by the resistance ratio of resistance 20 and resistor 24, and is thus proportional to the resistance of the resistor 21, that is, as a linear function of temperature. An adder section F comprises an operational amplifier 25, which adds the voltages at the terminals 19 and 22, and outputs a value of enthalpy expressed by equation (K) as a voltage from a terminal 26.

In calculating the enthalpy according to formula (C), it is necessary that the temperature signal t and humidity signal $\phi$ be respectively proportional to the temperature and humidity of the object being measured. The means for generating such humidity signals and temperature signals are shown in FIGS. 10 and 11.

Figure 10:
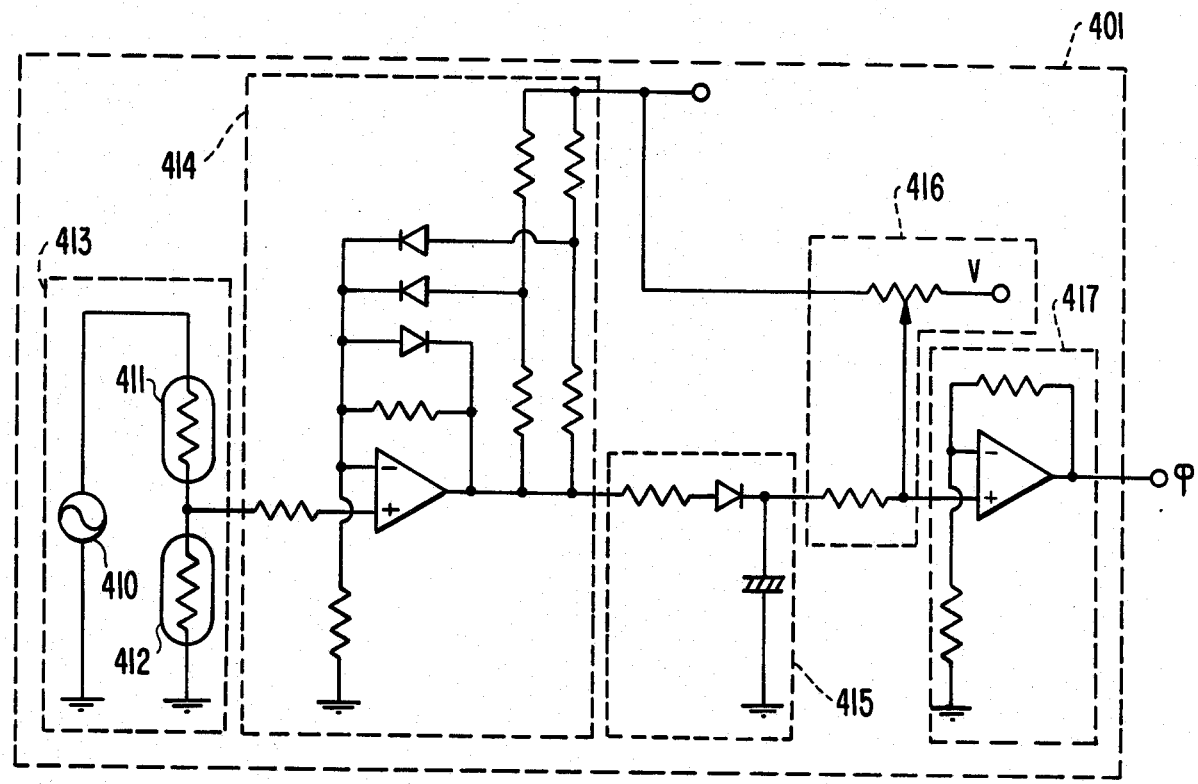
FIGS. 10 and 11 respectively show humidity and temperature signal generators.

FIG. 10 is an example of the construction of a humidity sensor 401, which is composed of a humidity detecting part 413, a polygonal approximating part 414, a rectifying and smoothing part 415, a bias adjusting part 416, and an amplifier 417. The temperature detecting part 413 is a series circuit of AC power supply 410, and a humidity sensing resistance element 411 and a temperature sensing resistance element 412, and the humidity signal picks up the voltage across the temperature sensing resistance element 412. This temperature sensing resistance element 412 is used to compensate for the temperature characteristics of the humidity sensing resistance element. Similarly, it is due to the characteristic of the humidity sensing resistance element 411 that a humidity signal is obtained from the temperature sensing resistance element 412 which is serially connected to the humidity sensing resistance element 411. It is the characteristic of the element that the resistance of the element decreases as the ambient relative humidity rises. On the other hand, the required humidity signal is proportional to the relative humidity. It is possible to obtain a signal in a required direction from the terminal voltage of the temperature sensing element 412 which is connected serially to the humidity sensing resistance element 411. The humidity signal detected by the humidity detecting part 413 is corrected into a relationship expressing the relative humidity and the resistive humidity signal as a linear equation by the polygonal approximating part 414. The output of this polygonal approximating part 414, which is an AC signal, is converted into a DC signal by the rectifying and smoothing part 425 in the next stage. The bias adjusting part 416 is used to adjust the zero point of the humidity signal from the rectifying and smoothing part 415, and as a result of this adjustment, the humidity signal becomes a value proportional to the ambient relative humidity of the humidity sensing resistance element 411. The amplifier 417 is used to amplify the humidity signal up to a required signal level.

Figure 11:
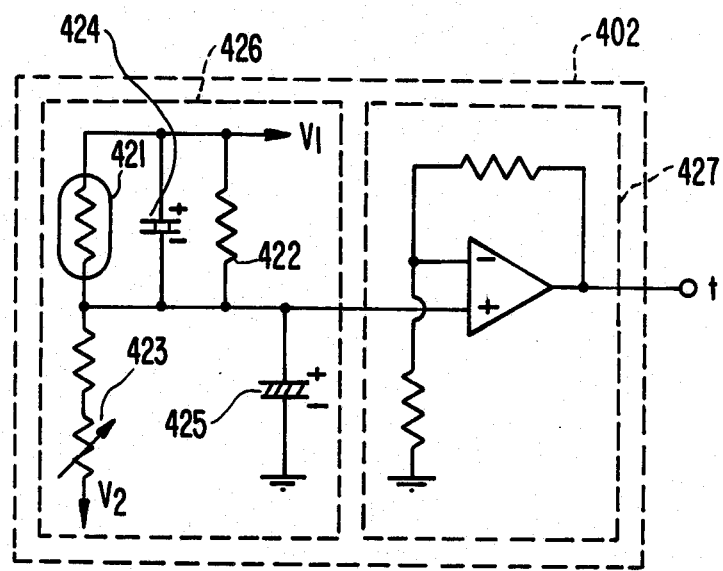

A practical structure of the temperature sensor 402 is shown in FIG. 11. The temperature sensor 402 is composed of temperature a detecting part 426, and an amplifier 427, and it detects the ambient temperature, and outputs a temperature signal proportional to it. The temperature detecting part 426 is composed of temperature sensing resistance element 421, and a parallel resistance 422, and a series resistance 423, and noise suppressing capacitors 424 and 425, and power supplies $V_1$ and $V_2$. As the temperature sensing resistance element 421 responds to the ambient temperature, the resistance changes, and a temperature signal proportional to the ambient temperature is output. This temperature signal is amplified by the amplifier 427, and a necessary temperature signal is obtained.

Furthermore, an embodiment to enthalpy output calculator which performs the calculation expressed in formula (C) is described by referring to FIGS. 8 to 11.

Figure 8:
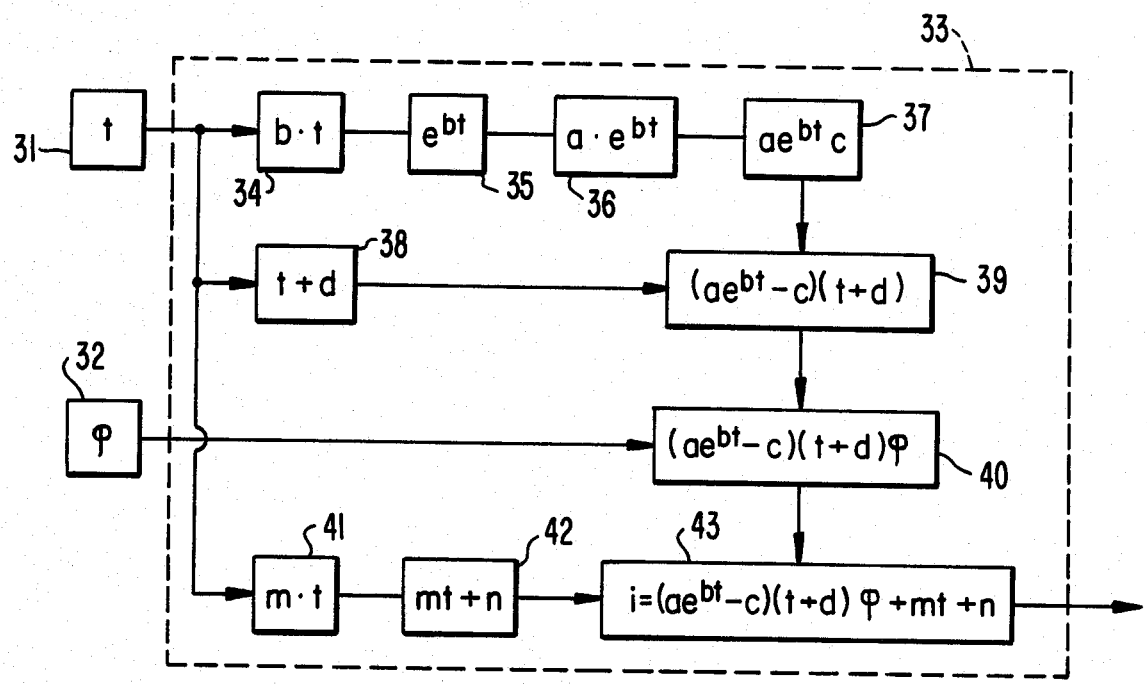
FIG. 8 is an embodiment of this invention.

FIG. 8 shows a basic structure of an embodiment according to this invention. Element 31 is a temperature sensor which outputs a temperature signal proportional to the temperature of a body of gas. Element 32 is a humidity sensor which outputs a humidity signal proportional to the temperature of said body of gas, and element 33 is an enthalpy calculating means which is composed of first to fifth multiplying means, first to third adding means, a subtracting means, and an exponential function calculating means.

Element 34 is a first multiplying means which multiplies the temperature signal t from the temperature detecting part by constant b, and obtains an output bt. Element 35 is an exponential function calculating means which calculates the exponential function on the output signal of said first multiplying means 34 and obtains as an output $e^{bt}$. Element 36 is a second multiplying means which calculates the product of output of said exponential function calculating means 35 and constant a and output $a \cdot e^{bt}$. Element 37 is a subtracting means, which calculates the difference between the output of said second multiplying means 36 and constant c, and obtains as an output ($a \cdot e^{bt} - c$). Element 38 is a first adding means which adds the output temperature signal t of the temperature sensor 31 and constant d and obtains as an output (t+d). Element 39 is a third multiplying means which multiplies the signal ($a \cdot e^{bt} - c$) of said subtracting means 37 and the signal of said first adding means and obtains as an output ($a \cdot e^{bt} - c$)(t+d). Element 40 is a fourth multiplying means which multiplies the output of said third multiplying means 39 and the humidity signal $\phi$ of humidity sensor and obtains as an output ($a \cdot e^{bt} - c$)(t+d)$\phi$. Element 41 is a fifth multiplying means which multiplies the temperature signal t from temperature sensor 31 and constant m and delivers as an output (m·t). Element 42 is a second adding means which adds the output (m·t) of said fifth multiplying means and constant n and delivers as an output (mt+n). Element 43 is a third adding means which adds the output ($a \cdot e^{bt} - c$)(t+d)$\phi$ of said fourth multiplying means and the output (mt+n) of said second adding means and outputs a signal corresponding to the enthalpy of the measured body of gas. This enthalpy calculating means may be realized by using either electronic circuitry or a microcomputer. In particular, when using a microcomputer for both the control of an air-conditioning system and the calculation of the enthalpy, the arithmetic capacity of the microcomputer is sufficient, and by a simple method of adding a program to the microcomputer, the high precision control of air-conditioning is possible while calculating the enthalpy at a high accuracy, and the overall cost may be reduced at the same time.

Figure 9:
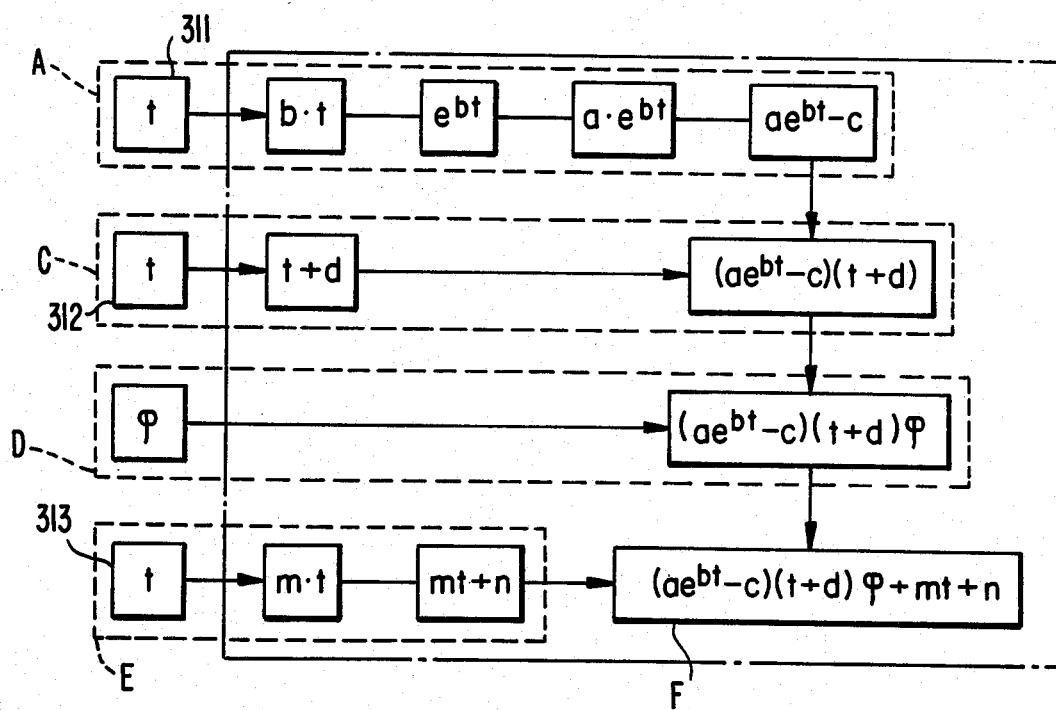
FIG. 9 shows the temperature sensor 31 of FIG. 8.

FIG. 9 shows the temperature sensor 31 in FIG. 8 divided into a first temperature sensor 311, and a second temperature sensor 312, and third temperature sensor 313. This purpose is to construct the multiplying means using simple electronic circuits in order to obtain enthalpy output signals at a low cost and high precision.

In FIG. 9, part A is a first temperature sensor, which includes an exponential function part B. Part C is a second temperature sensor including multiplying means. Part D is a relative humidity sensor including multiplying means.

Figure 7:
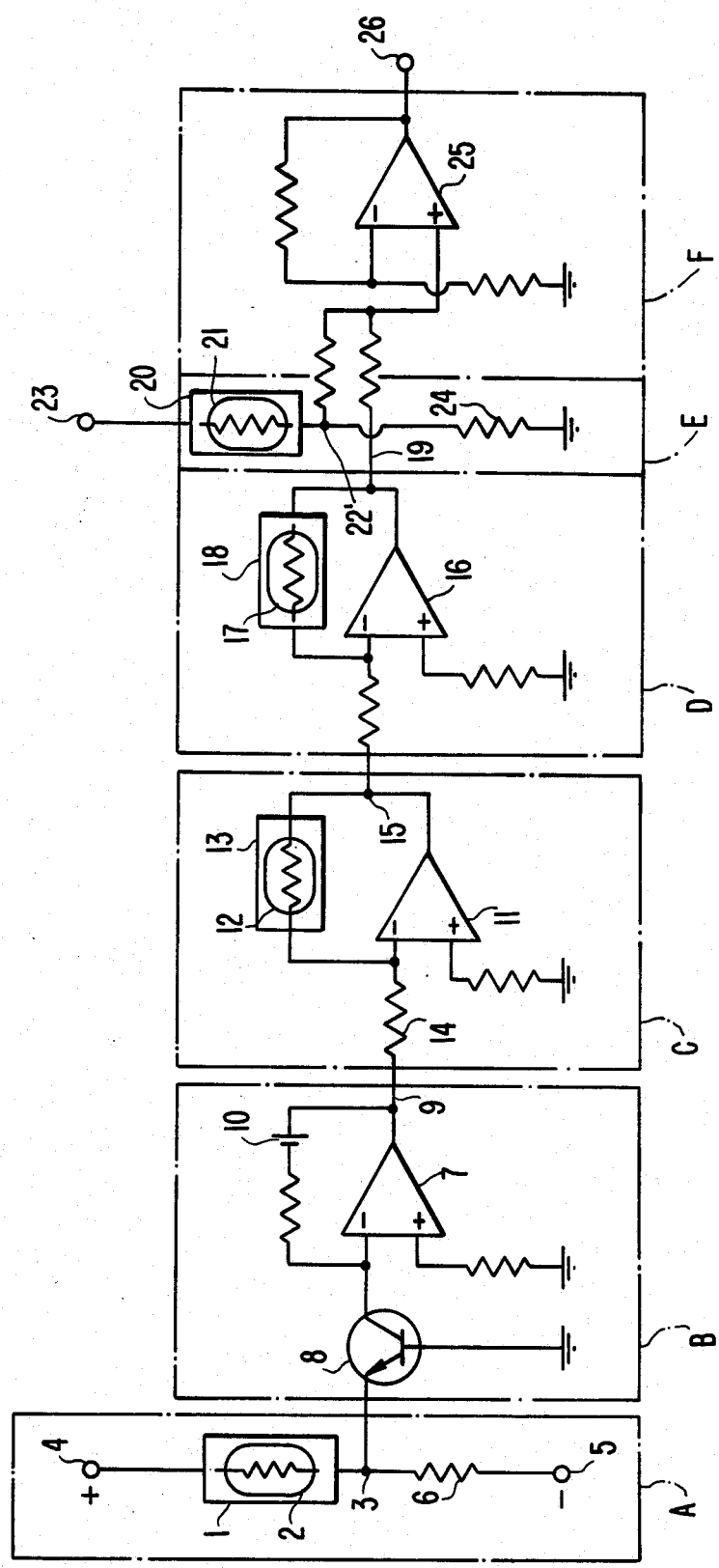

Part E is a third temperature sensor and Part F is an adding unit, which respectively correspond to the same symbols used in FIG. 7.

As has been described, in an enthalpy output unit according to this invention, the calculations depend on simple equations in which the variables employed are the dry bulb temperature and the relative humidity, which are the most important factors for an index of environmental conditions and, therefore, the calculations can be performed directly by sensing only the dry bulb temperature and the relative humidity, without needing to determine other factors such as the saturated vapor pressure, by the use of approximate expressions or conversion tables. The equation according to this invention enables an easy, very accurate calculation when using an electronic computer. Also, since the use of arithmetic unit according to this invention permits the calculation of a value of enthalpy as a measure of the heat energy contained in the air on the basis of temperature and relative humidity which are the direct objects of air conditioning, many advantages such as its application to an automatic control of air conditioning, and the provision of a simple calculation circuit with few components, are thereby provided.

What is claimed is:

1. An enthalpy calculator unit for outputting a signal corresponding to the enthalpy of a body of gas comprising: a temperature sensor for detecting the dry bulb temperature of the body of gas and for outputting an electrical signal corresponding thereto;

a humidity sensor for detecting the relative humidity of said body of gas and for outputting an electrical signal corresponding thereto;

a first multiplying means for multiplying said signal output from said temperature sensor by a constant b and for outputting an electrical signal corresponding thereto;

an exponential function operating means for calculating the exponential function of said output from said multiplying means and outputting an electrical signal corresponding thereto;

a second multiplying means for multiplying said output from said exponential function operating means by a constant a and for outputting a signal corresponding thereto;

a subtracting means for subtracting a constant c from said output from said second multiplying means and for outputting a signal corresponding thereto;

a first adding means for adding a constant d to said output from said temperature sensor and for outputting a signal corresponding thereto;

a third multiplying means for multiplying said output from said subtracting means by said output from said first adding means and for outputting a signal corresponding thereto;

a fourth multiplying means for multiplying said output from said humidity sensor by said output from said third multiplying means and for outputting a signal corresponding thereto;

a fifth multiplying means for multiplying said output from said temperature sensor by a constant m and for outputting a signal corresponding thereto;

a second adding means for adding a constant n to said output from said fifth multiplying means and for outputting a signal corresponding thereto; and a third adding means for said output from said second adding means and said output from said fourth multiplying means and for outputting a signal corresponding thereto, said output corresponding to the enthalpy of said body of gas.

* * * * *